(12) United States Patent
Kim et al.

(10) Patent No.: US 11,504,088 B2
(45) Date of Patent: Nov. 22, 2022

(54) ULTRASONIC PROBE

(71) Applicant: SAMSUNG MEDISON CO., LTD., Gangwon-do (KR)

(72) Inventors: Yong Jae Kim, Gyeongju-si (KR); Jong-Sun Ko, Seoul (KR); Jae-Yk Kim, Seongnam-si (KR)

(73) Assignee: SAMSUNG MEDISON CO. LTD., Gangwon-Do (KR)

( * ) Notice: Subject to any disclaimer, the term of this patent is extended or adjusted under 35 U.S.C. 154(b) by 313 days.

(21) Appl. No.: 16/301,393

(22) PCT Filed: Apr. 4, 2017

(86) PCT No.: PCT/KR2017/003686
§ 371 (c)(1),
(2) Date: Nov. 13, 2018

(87) PCT Pub. No.: WO2017/195983
PCT Pub. Date: Nov. 16, 2017

(65) Prior Publication Data
US 2020/0315576 A1   Oct. 8, 2020

(30) Foreign Application Priority Data
May 10, 2016 (KR) .................. 10-2016-0056772

(51) Int. Cl.
*A61B 8/00* (2006.01)
*B06B 1/06* (2006.01)

(52) U.S. Cl.
CPC .......... *A61B 8/4444* (2013.01); *A61B 8/4494* (2013.01); *B06B 1/067* (2013.01)

(58) Field of Classification Search
CPC ................ A61B 8/4444; A61B 8/4494; A61B 2562/166; A61B 8/00; B06B 1/067; H01L 41/113
See application file for complete search history.

(56) References Cited

U.S. PATENT DOCUMENTS

2002/0073781 A1   6/2002   Hashimoto et al.
2009/0034370 A1*  2/2009   Guo ..................... G10K 11/002
                                                    29/25.35
(Continued)

FOREIGN PATENT DOCUMENTS

EP     2230029 A1      9/2010
JP     2001-276060 A   10/2001
(Continued)

OTHER PUBLICATIONS

European Office Action dated Aug. 2, 2021 issued in European Patent Application No. 17796283.4.
(Continued)

*Primary Examiner* — Joseph M Santos Rodriguez
*Assistant Examiner* — Kaitlyn E Sebastian
(74) *Attorney, Agent, or Firm* — Morgan, Lewis & Bockius LLP

(57) ABSTRACT

Disclosed herein is an ultrasonic probe including a piezoelectric layer, a matching layer disposed at an upper portion of the piezoelectric layer, a conductive member disposed at a lower portion of the piezoelectric layer, a second connector coupled to at least one side of the conductive member, and a printed circuit board coupled to a side of the second connector and electrically coupled to the second connector. A printed circuit board is disposed outside a laminated structure of the acoustic element so that the printed circuit board can be prevented from affecting acoustic characteristics of the ultrasonic probe, a failure in a process of manufacturing the ultrasonic probe that occurs due to a change in temperature or humidity can be prevented, and the manufacturing process can be relatively simplified.

12 Claims, 15 Drawing Sheets

(56) References Cited

U.S. PATENT DOCUMENTS

| | | | |
|---|---|---|---|
| 2009/0069689 A1 | 3/2009 | Isono | |
| 2010/0103637 A1* | 4/2010 | Jin | A61B 8/4494 361/777 |
| 2010/0241004 A1* | 9/2010 | Jung | A61B 8/4444 600/459 |
| 2011/0105906 A1* | 5/2011 | Lee | G10K 11/004 600/459 |
| 2011/0121687 A1* | 5/2011 | Aoki | B06B 1/0677 310/334 |
| 2012/0056512 A1* | 3/2012 | Jin | G10K 11/004 310/335 |
| 2012/0149228 A1* | 6/2012 | Matsumoto | H01R 13/4223 439/329 |
| 2013/0231566 A1* | 9/2013 | Jin | B06B 1/06 600/459 |
| 2014/0350407 A1 | 11/2014 | Chaggares et al. | |
| 2015/0011881 A1* | 1/2015 | Okuda | G10K 11/002 600/443 |
| 2015/0018687 A1 | 1/2015 | Osawa | |
| 2016/0007964 A1* | 1/2016 | Ona | G01S 15/8927 600/459 |

FOREIGN PATENT DOCUMENTS

| | | |
|---|---|---|
| JP | 2013176537 A | 9/2013 |
| KR | 10-2010-0112104 A | 10/2010 |

OTHER PUBLICATIONS

Extended European Search Report dated Nov. 29, 2019 issued in European Patent Application No. 17796283.4.
Written Opinion and International Search Report dated Jun. 14, 2017 issued in International Patent Application No. PCT/KR2017/003686 (with English translation).

* cited by examiner

ELEVATION DIRECTION

ELEVATION DIRECTION

ELEVATION DIRECTION

ELEVATION DIRECTION

ELEVATION DIRECTION

ELEVATION DIRECTION

ELEVATION DIRECTION (a)

(b)

(c)

ULTRASONIC PROBE

CROSS REFERENCE

This patent application is the U.S. National Phase under 35 U.S.C. § 371 of International Application No. PCT/KR2017/003686, filed on Apr. 4, 2017, which claims the benefit of Korean Patent Application No. 10-2016-0056772, filed on May 10, 2016, the entire contents of each are hereby incorporated by reference.

TECHNICAL FIELD

The present invention relates to an ultrasonic probe that generates an image of an inside of an object by using ultrasonic waves, and more particularly, to an ultrasonic probe structure in which a printed circuit board inside an ultrasonic probe is disposed outside a laminated structure of an acoustic element.

BACKGROUND ART

An ultrasonic diagnostic apparatus refers to an apparatus that radiates an ultrasonic signal toward a target area of an object, receives an ultrasonic signal (echoed ultrasonic signal) reflected from the object, and uses information thereon to non-invasively obtain an image related to a cross-section or blood flow of a soft tissue.

The ultrasonic diagnostic apparatus has advantages over other diagnostic imaging apparatuses, such as an X-ray diagnostic apparatus, an X-ray computerized tomography (CT) scanner, a magnetic resonance imaging (MRI) apparatus, and a nuclear medicine diagnostic apparatus, in that the ultrasonic diagnostic apparatus is relatively small and inexpensive. In addition, the ultrasonic diagnostic apparatus is capable of acquiring an image related to an inside of an object in real time and has high safety due to not causing exposure to radiation. Therefore, generally, the ultrasonic diagnostic apparatus has been widely used in cardiac diagnosis, abdominal diagnosis, urologic diagnosis, and obstetric and gynecologic diagnosis of people.

Therefore, the ultrasonic diagnostic apparatus includes an ultrasonic probe for transmitting an ultrasonic signal to an object in order to obtain an ultrasound image of an inside of the object and receiving an echoed ultrasonic signal reflected from the object.

The ultrasonic probe includes an acoustic element. The acoustic element includes a piezoelectric layer configured to convert an electrical signal to an acoustic signal and vice versa as a piezoelectric material vibrates, a matching layer configured to reduce an acoustic impedance difference between the piezoelectric layer and an object so that ultrasonic waves generated from the piezoelectric layer are effectively transmitted to the object, a lens configured to focus ultrasonic waves traveling toward the front of the piezoelectric layer to a specific point, and a backing layer configured to block ultrasonic waves traveling toward the rear of the piezoelectric layer so that image distortion is prevented.

Examples of an internal structure of the ultrasonic probe according to the related art include a bonding structure and a focused ion beam (FIB) structure.

The bonding structure refers to a structure in which a ground printed circuit board (GND PCB) and a signal printed circuit board (SIG PCB) are respectively inserted into electrodes formed at an upper portion and a lower portion of a piezoelectric layer and the GND PCB and the SIG PCB are parallel to a laminated structure of an acoustic element. The FIB structure refers to a structure in which a GND PCB and SIG PCB are inserted into a backing layer to be perpendicular to a laminated structure of an acoustic element and are respectively connected to electrodes formed at an upper portion and a lower portion of a piezoelectric material.

DISCLOSURE

Technical Problem

However, in the case of an ultrasonic probe having a bonding structure, an acoustic characteristic of the ultrasonic probe is affected by a material and/or thickness of a printed circuit board (PCB), and especially in the case of a probe using a high frequency, there is a problem in that acoustic characteristics such as a frequency and sensitivity are significantly changed according to a thickness of a copper (Cu) foil of a PCB. In addition, there is a limitation in reducing a thickness of the Cu foil of the PCB due to a problem in terms of manufacture and processing of the PCB itself or the ultrasonic probe.

In addition, in the case of a focused ion beam (FIB) structure, there may be a problem in that a PCB, which is disposed inside a backing layer of an ultrasonic probe, contracts or expands according to changes in temperature and humidity, and this may cause a problem in that a failure is caused in a process in which an acoustic element is divided into a plurality of acoustic elements during a process of manufacturing the ultrasonic probe.

The present invention has been devised to solve the above-described problems of the related art. Unlike the conventional ultrasonic probe in which a PCB of the ultrasonic probe is inserted into a laminated structure of an acoustic element in parallel or is included inside a backing layer, an ultrasonic probe according to the present invention is disposed outside so that a PCB is prevented from affecting acoustic characteristics of the ultrasonic probe, and a manufacturing process is not affected by structural characteristics of an inside of the ultrasonic probe.

Technical Solution

An ultrasonic probe according to an embodiment of the present invention includes a piezoelectric layer, a matching layer disposed at an upper portion of the piezoelectric layer, a conductive member disposed at a lower portion of the piezoelectric layer, a second connector coupled to at least one side of the conductive member, and a printed circuit board coupled to a side of the second connector and electrically coupled to the second connector.

The printed circuit board may be disposed outside a laminated structure of the piezoelectric layer, the matching layer, and the conductive member.

The conductive member may be formed of an enhanced layer configured to totally reflect an acoustic signal.

The enhanced layer may include tungsten.

The conductive member may be formed of a backing layer configured to absorb or attenuate an acoustic signal.

The conductive member may include a conductive material.

An electrode for electrical conduction may be formed at an outer circumferential surface of the conductive member.

The electrode may be formed using a sputtering method.

The second connector may be formed of the same material as the conductive member.

The printed circuit board may include a flexible printed circuit board.

The printed circuit board may include at least one hole through which the second connector passes.

The hole may be electrically connected to a circuit configuration of the printed circuit board.

The printed circuit board may include at least one slot through which the second connector passes.

The slot may be electrically connected to a circuit configuration of the printed circuit board.

The printed circuit board may include a plurality of concave-convex portions to which the second connector is fitted.

The printed circuit board may include one or more hole lands coupled to the second connector.

The lands may be a copper foil layer which is larger than the hole and formed along a circumference of the hole at an outer wall of the printed circuit board.

The printed circuit board may include one or more pads coupled to the second connector.

The pad may be a copper foil layer formed at an outer wall of the printed circuit board.

The printed circuit board may further include an engaging portion through which at least a portion of the second connector is inserted into the printed circuit board.

The matching layer may include a conductive material.

The matching layer may be formed of a non-conductive material, and an electrode for electrical conduction may be formed at an outer circumferential surface of the non-conductive material.

The electrode may be formed using a sputtering method.

A first connector may be formed of the same material as the matching layer.

The first connector may be coupled to an outer wall of the printed circuit board and formed as a copper foil layer.

The first connector may include an electrical connection means so that the matching layer and the printed circuit board are electrically coupled.

The first connector may include at least one of a gasket, a conductive film, a conductive tape, a conductive adhesive, a conductive epoxy, and a conductive elastomer.

The first connector may be coupled to the matching layer and the outer wall of the printed circuit board by using an adhesive member.

The second connector may be coupled to the conductive member and the printed circuit board by using an adhesive member.

The adhesive member may include at least one of a conductive adhesive, a conductive epoxy, a conductive tape, and a conductive solder.

The present invention may further include a supporter coupled to the printed circuit board and configured to support the printed circuit board to be fixed to a side of the laminated structure of the piezoelectric layer, the matching layer, and the conductive member.

The supporter may be disposed at a lower portion of the conductive member.

The supporter may include at least one of a bolt, a clip, a gasket, a spacer, and a pin.

Advantageous Effects

In a structure of an acoustic element inside an ultrasonic probe, a printed circuit board is disposed outside a laminated structure of the acoustic element so that the printed circuit board can be prevented from affecting acoustic characteristics of the ultrasonic probe, a failure in a process of manufacturing the ultrasonic probe that occurs due to a change in temperature or humidity can be prevented, and the manufacturing process can be relatively simplified.

Figure 8:
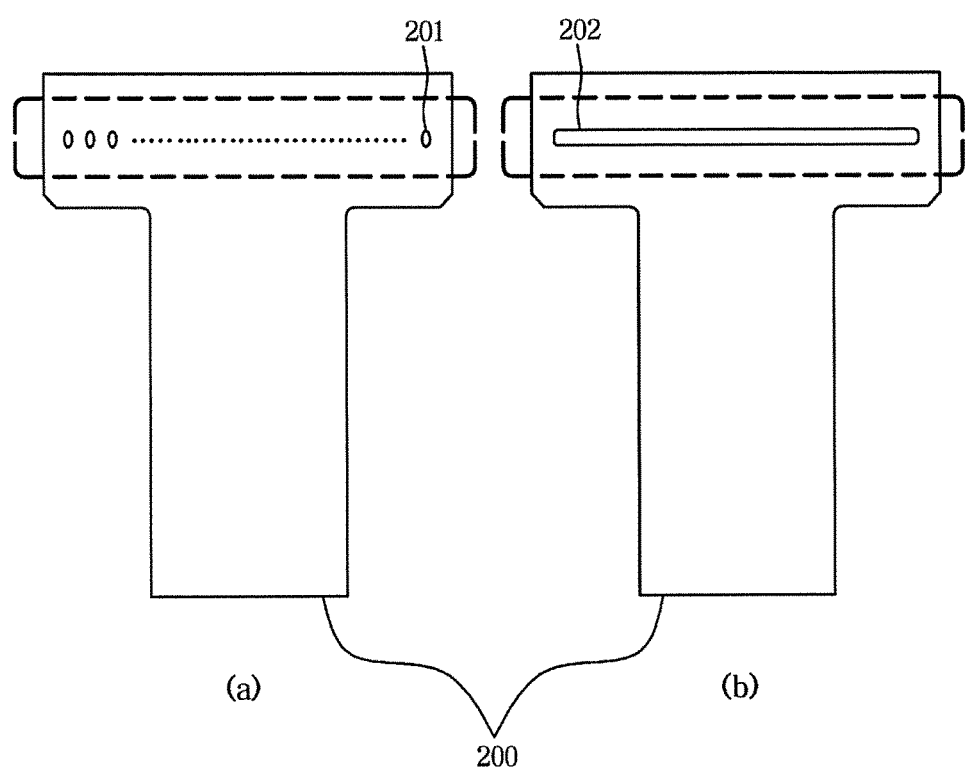

(a) and (b) of FIG. 8 are views illustrating states of a printed circuit board according to still another embodiment of the present invention.

Figure 9:
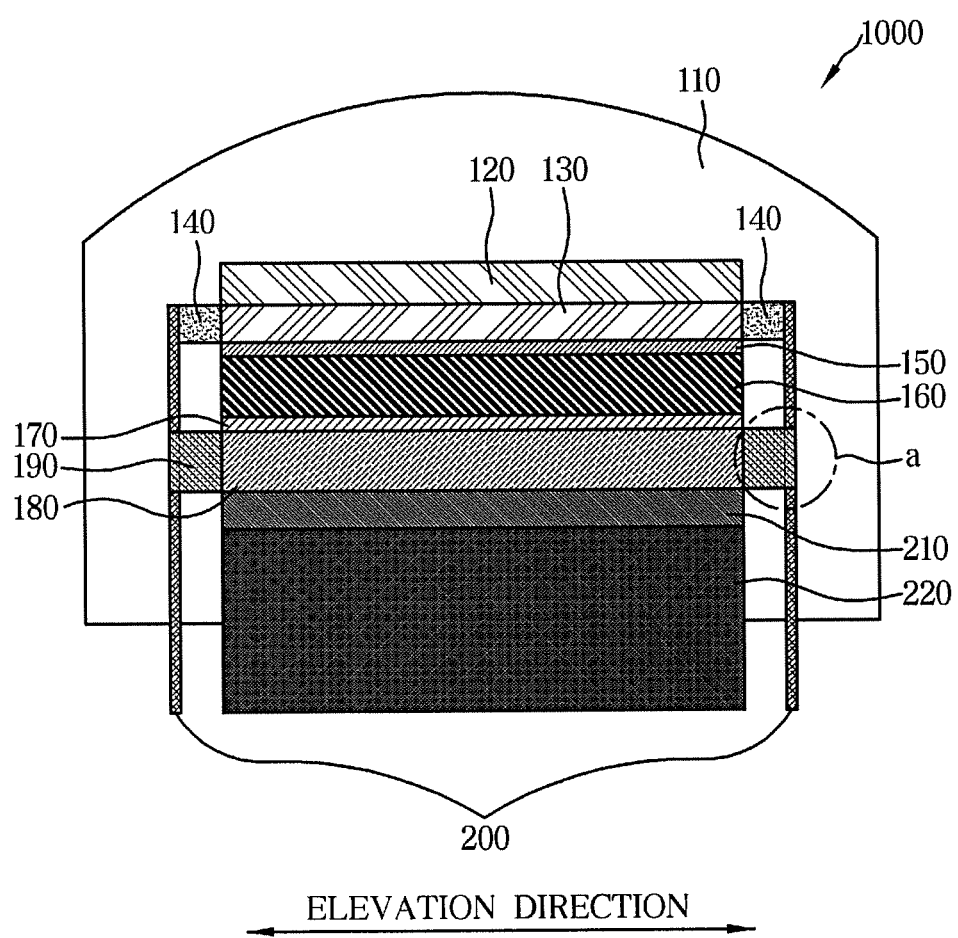

FIG. 9 is a view illustrating a laminated structure of an acoustic element of an ultrasonic probe according to yet another embodiment of the present invention.

Figure 10:
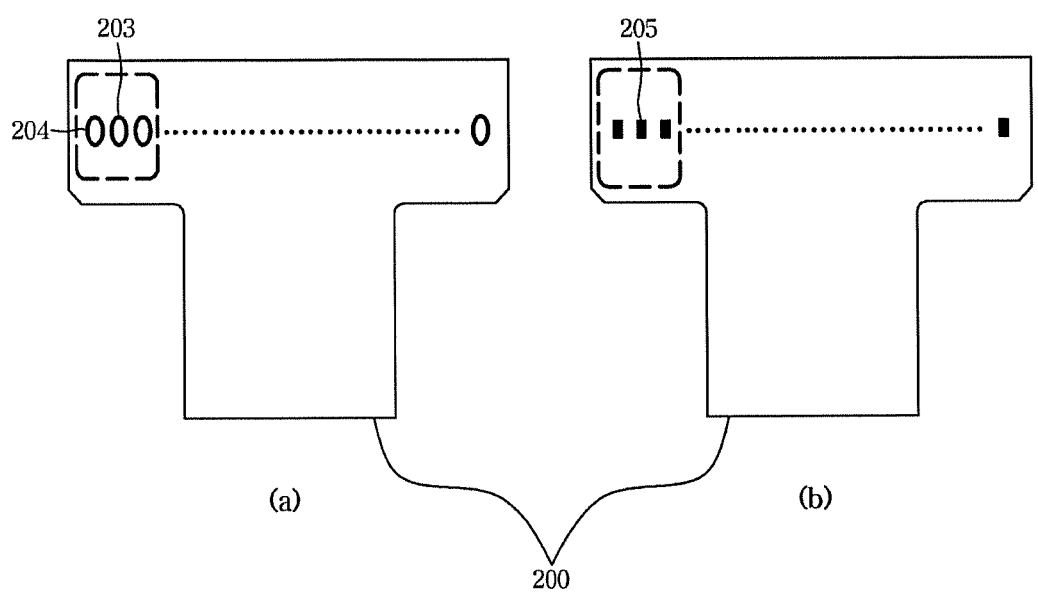

(a) and (b) of FIG. 10 are views illustrating states of a printed circuit board according to yet another embodiment of the present invention.

Figure 11:
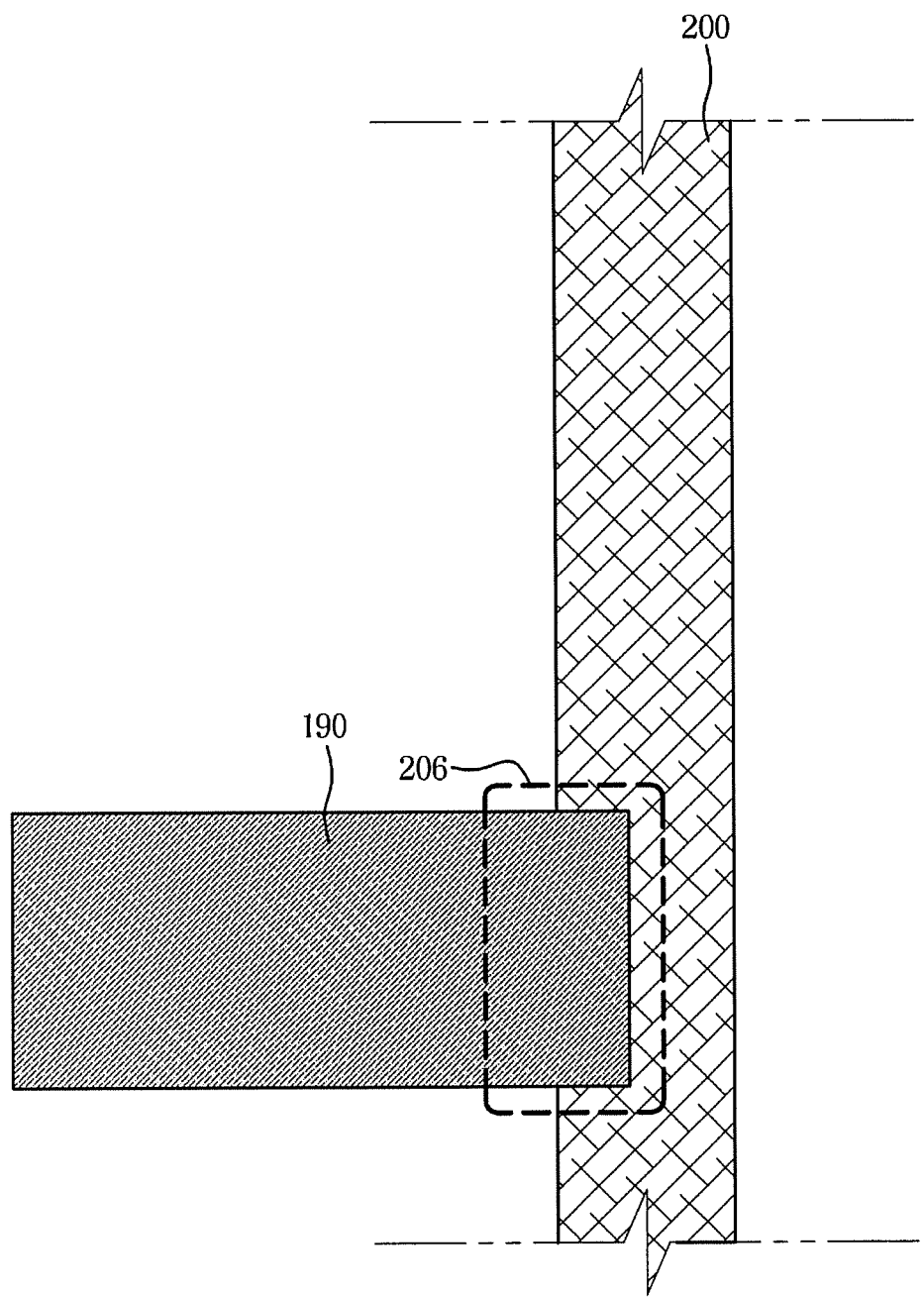

FIG. 11 is a view illustrating a state in which a second connector is inserted into a printed circuit board according to yet another embodiment of the present invention.

Figure 12:
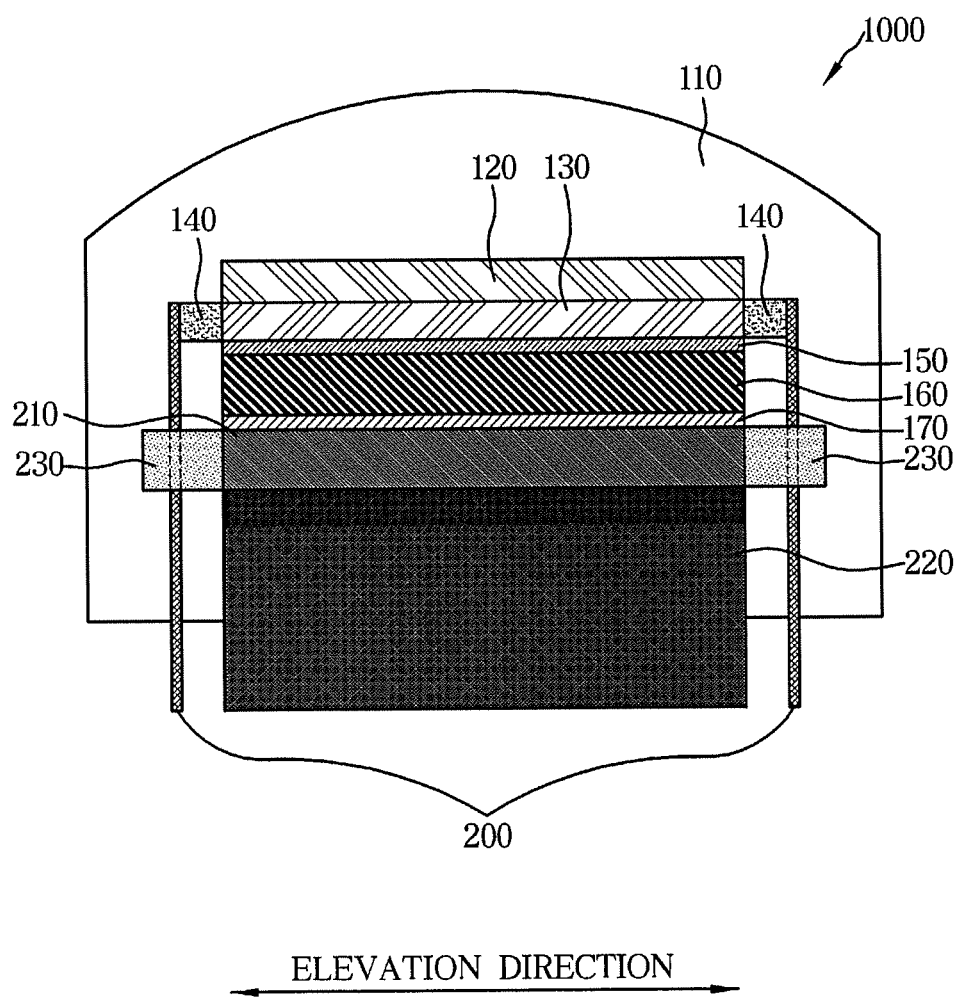

FIG. 12 is a view illustrating a laminated structure of an acoustic element of an ultrasonic probe according to yet another embodiment of the present invention.

Figure 13:
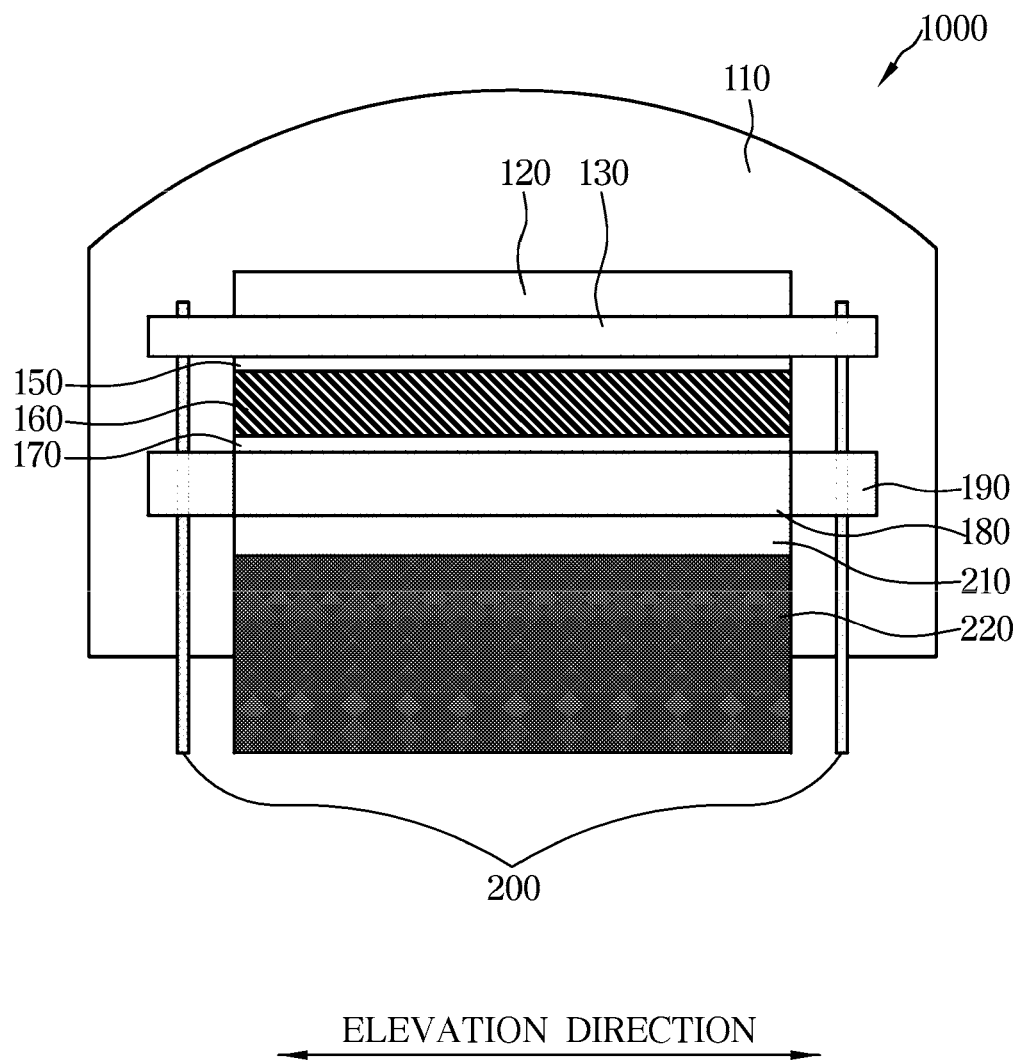

FIG. 13 is a view illustrating a laminated structure of an acoustic element of an ultrasonic probe according to yet another embodiment of the present invention.

Figure 14:
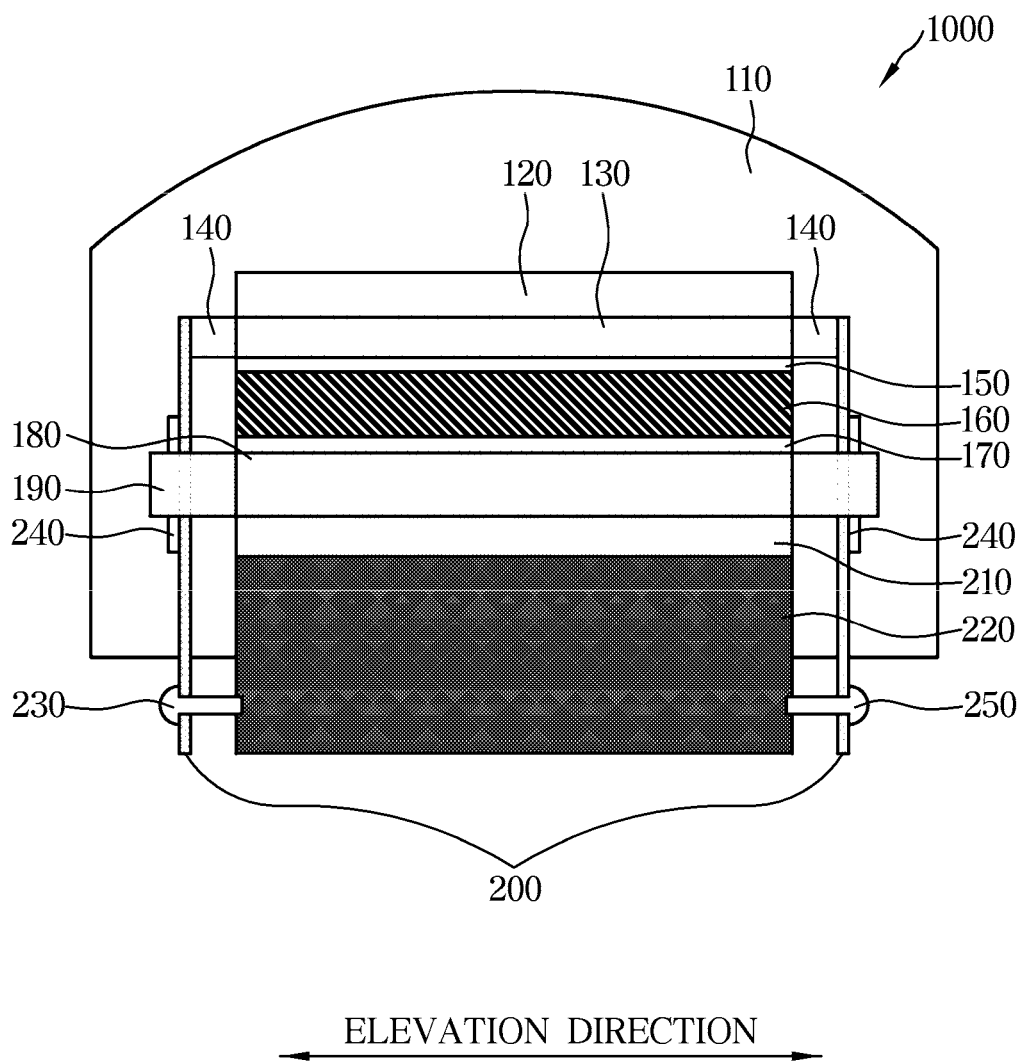

FIG. 14 is a view illustrating a laminated structure of an acoustic element of an ultrasonic probe according to yet another embodiment of the present invention.

Figure 15:
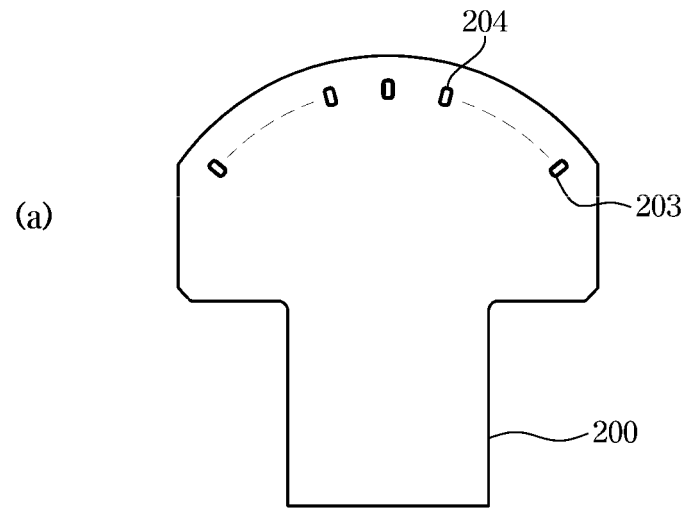
Figure 15:
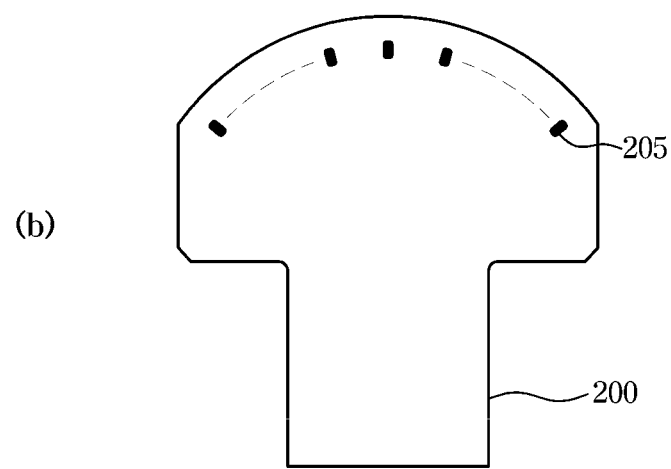
Figure 15:
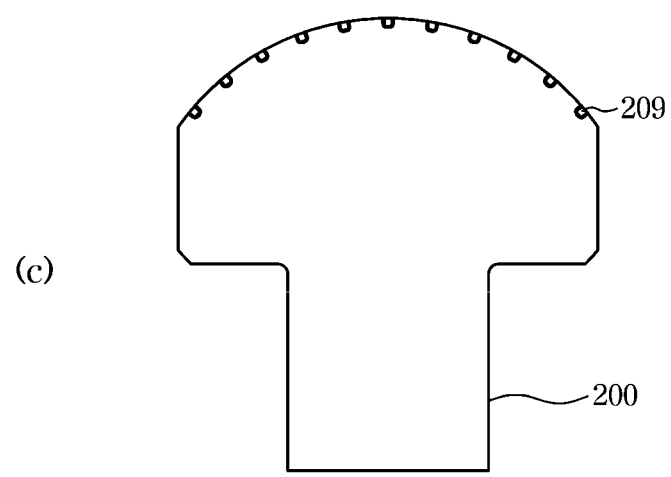

(a) to (c) of FIG. 15 are views illustrating states of a printed circuit board according to yet another embodiment of the present invention.

MODES OF THE INVENTION

Various embodiments described herein and configurations illustrated in the drawings are merely exemplary embodiments of the present invention, and various modifications which may replace the embodiments and the drawings herein may be present at the time of filing this application.

In addition, terms used herein are for describing the embodiments and are not intended to limit and/or restrict the invention disclosed herein. A singular expression includes a plural expression unless context clearly indicates otherwise.

In the application, terms such as "include" or "have" should be understood as designating that features, number, steps, operations, elements, parts, or combinations thereof exist and not as precluding the existence of or the possibility of adding one or more other features, numbers, steps, operations, elements, parts, or combinations thereof in advance.

Terms including ordinals such as "first" and "second" used herein may be used to describe various elements, but the elements are not limited by the terms. The terms are only used for the purpose of distinguishing one element from another element. For example, a first element may be referred to as a second element while not departing from the scope of the present invention, and likewise, a second element may also be referred to as a first element. The term "and/or" refers to a combination of a plurality of related elements that have been described or any one element among the plurality of related elements that have been described.

Hereinafter, structural features and effects of the present invention will be described in detail with reference to the accompanying drawings.

Figure 1:
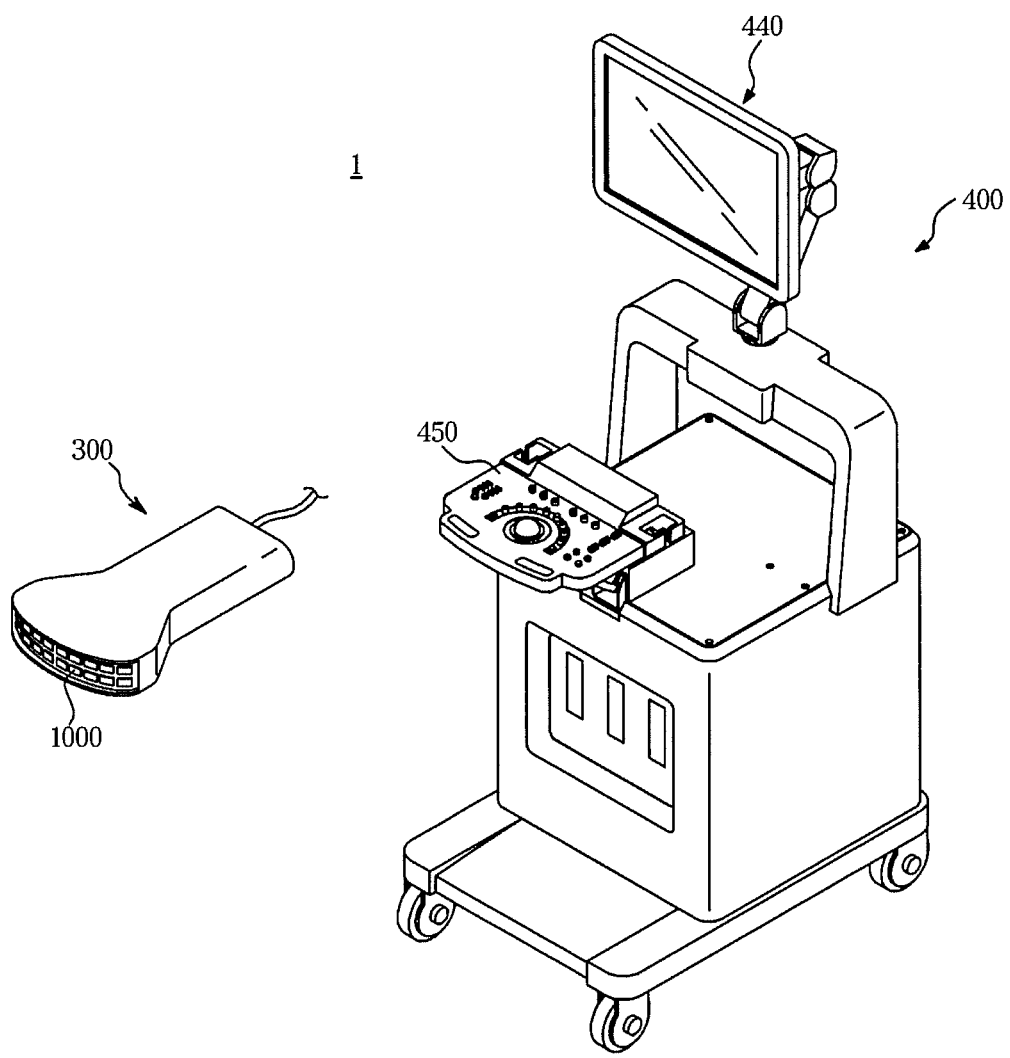
FIG. 1 is a view illustrating an external configuration of an ultrasonic diagnostic apparatus which includes an ultrasonic probe according to an embodiment of the present invention.

FIG. 1 is a view illustrating an external configuration of an ultrasonic diagnostic apparatus according to an embodiment of the present invention.

Referring to FIG. 1, an ultrasonic diagnostic apparatus 1 includes an ultrasonic probe 300 configured to transmit an ultrasonic signal to an object (not illustrated), receive an echoed ultrasonic signal from the object (not illustrated), and convert the received echoed ultrasonic signal to an electrical signal and a main body 400, which is a system configured to generate a diagnostic image on the basis of the received ultrasonic signal. The main body 400 may be connected to the ultrasonic probe 300 via a wired or wireless communication mode, and the mode of connection is not limited to any specific mode.

According to an embodiment of the present invention, the ultrasonic probe 300 may be connected to the main body 400 via a wireless or wired communication network and receive various signals required for controlling the ultrasonic probe 300 or transmit an analog signal or a digital signal corresponding to an echoed ultrasonic signal that the ultrasonic probe 300 has received.

Meanwhile, the wireless communication network refers to a communication network via which signals may be transmitted and received wirelessly. The main body 400 may perform wireless communication with the ultrasonic probe 300 via at least one of a short range communication module and a mobile communication module.

The short range communication module refers to a module for short range communication within a predetermined distance. Examples of a short range communication technology may include a wireless local area network (LAN), wireless fidelity (Wi-Fi), Bluetooth, ZigBee, Wi-Fi Direct (WFD), ultra wideband (UWB), infrared data association (IrDA), Bluetooth low energy, and near-field communication (NFC), but the short range communication technology is not limited thereto.

The mobile communication module may transmit and receive a wireless signal to and from at least one of a base station, an external terminal, and a server in a mobile communication network. Here, the wireless signal refers to a signal including various forms of data. That is, the main body 400 may transmit and receive a signal including various forms of data to and from the ultrasonic probe 300 via at least one of a base station and a server.

For example, the main body 400 may transmit and receive a signal including various forms of data to and from the ultrasonic probe 300 via a base station using a mobile communication network such as third generation (3G) and fourth generation (4G).

The main body 400 may transmit and receive data to and from a hospital server connected thereto via a picture archiving and communication system (PACS) or to and from another medical apparatus in the hospital. In addition, the main body 400 may transmit and receive data according to the digital imaging and communications in medicine (DICOM) standard. However, embodiments are not limited thereto.

In addition, the main body 400 may transmit and receive data to and from the ultrasonic probe 300 via a wired communication network. The wired communication network refers to a communication network via which signals may be transmitted and received via a wire.

According to an embodiment, the main body 400 may transmit and receive various signals to and from the ultrasonic probe 300 using a wired communication network such as peripheral component interconnect (PCI), PCI-express, and universal serial bus (USB), but is not limited thereto.

Meanwhile, the main body 400 may include a display 440 and an input unit 450. The input unit 450 may receive various control commands and the like as well as settings information related to the ultrasonic probe 300 from a user.

According to an embodiment, the settings information related to the ultrasonic probe 300 includes gain information, zoom information, focus information, time gain compensation (TGC) information, depth information, frequency information, power information, frame average information, dynamic range information, and the like. However, the settings information related to the ultrasonic probe 300 is not limited to this embodiment and may include various other pieces of information that may be set to capture an ultrasound image.

The pieces of information may be transmitted to the ultrasonic probe 300 via a wireless communication network or a wired communication network, and the ultrasonic probe 300 may be set according to the received pieces of information. In addition, the main body 400 may receive various control commands, such as a command which requests that an ultrasonic signal be transmitted, from the user via the input unit 450 and transmit the received control commands to the ultrasonic probe 300.

Meanwhile, the input unit 450 may be implemented using a keyboard, a foot switch, or a foot pedal. For example, a keyboard may be implemented as hardware. Such a keyboard may include at least one of a switch, a key, a joystick, and a trackball. As another example, a keyboard may be implemented as software like a graphical user interface. In this case, the keyboard may be displayed on the display 440. A foot switch or a foot pedal may be provided at a lower portion of the main body 400, and the user may control an operation of the ultrasonic diagnostic apparatus 1 using the foot pedal.

The display 440 may be implemented using various known means such as a cathode ray tube (CRT), a liquid crystal display (LCD), a light emitting diode (LED), a plasma display panel (PDP), and an organic light emitting diode (OLED), but is not limited thereto.

The display 440 may display an ultrasound image of a target area inside an object. The ultrasound image displayed on the display 440 may be a two-dimensional ultrasound image or a three-dimensional ultrasound image. Various ultrasound images may be displayed according to an operation mode of the ultrasonic diagnostic apparatus 1. In addition, the display 440 may display information on an operation state of the ultrasonic probe 300 as well as menus or guides required for ultrasound diagnosis.

According to an embodiment, an ultrasound image not only includes an amplitude mode (A-mode) image, a brightness mode (B-mode) image, and a motion mode (M-mode) image, but also includes a color mode (C-mode) image and a Doppler mode (D-mode) image.

The A-mode image, which will be described below, refers to an ultrasound image showing an amplitude of an ultrasonic signal which corresponds to an echoed ultrasonic signal, the B-mode image refers to an ultrasound image showing the amplitude of the ultrasonic signal corresponding to the echoed ultrasonic signal using brightness, and the M-mode image refers to an ultrasound image showing motion of an object with time at a specific location. The D-mode image refers to an ultrasound image showing a moving object with waveforms using the Doppler effect, and the C-mode image refers to an ultrasound image showing the moving object in the form of color spectrum.

Meanwhile, when the display 440 is implemented as a touchscreen type, the display 440 may also perform the function of the input unit 450. That is, the main body 400 may receive various commands from the user via at least one of the display 440 and the input unit 450.

In addition, although not illustrated in the drawings, a voice recognition sensor may be provided in the main body 400 and receive a voice command from the user. A configuration of the ultrasonic probe will be described in more detail below.

Figure 2:
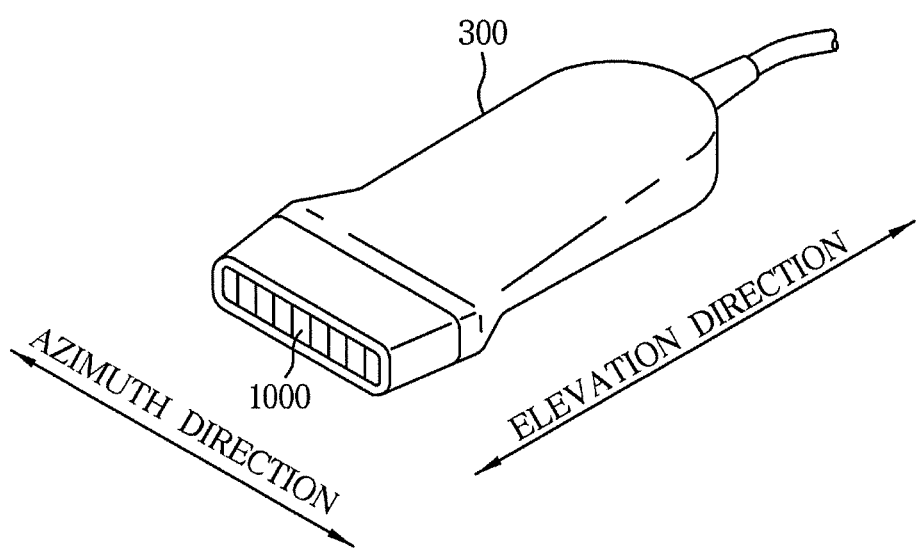
FIG. 2 is a view illustrating an internal structure of an ultrasonic probe including a plurality of arrays of acoustic elements according to an embodiment of the present invention.

FIG. 2 is a view illustrating an internal structure of an ultrasonic probe 300 including a plurality of arrays of acoustic elements 1000 according to an embodiment of the present invention.

The ultrasonic probe 300 may include the acoustic element 1000 configured to convert an electrical signal to an ultrasonic signal and vice versa so as to transmit the ultrasonic signal to an inside of an object (not illustrated).

More specifically, the ultrasonic probe 300 may serve to transmit an ultrasonic signal to a specific area inside the object (not illustrated) according to an electrical signal received from the main body 400, receive an echoed ultrasonic signal reflected from the specific area inside the object (not illustrated), and transmit the received echoed ultrasonic signal to the main body 400.

Meanwhile, the object (not illustrated) may be a living body of a human being or an animal, but is not particularly limited thereto. The object (not illustrated) may be anything as long as an internal structure thereof may be imaged using an ultrasonic signal.

In addition, the acoustic element 1000 may be configured in the form of a plurality of arrays in one dimension, and generally, a direction in which the acoustic element 1000 is divided into a plurality of acoustic elements 1000 and arranged is referred to as an azimuth direction, and a width direction of the acoustic element 1000, which is orthogonal to the direction in which the acoustic element 1000 is divided into a plurality of acoustic elements 1000 and arranged, is referred to as an elevation direction.

The ultrasonic probe 300 may generate an ultrasonic signal through the acoustic element 1000 and transmit the ultrasonic signal by focusing the ultrasonic signal to a specific target area inside the object (not illustrated), and the acoustic element 1000 may receive an echoed ultrasonic signal reflected from the specific target area inside the object (not illustrated).

When the reflected echoed ultrasonic signal is received by the acoustic element 1000, the acoustic element 1000 may vibrate with a predetermined frequency which corresponds to a frequency of the echoed ultrasonic signal, and accordingly, may output an alternating current of a frequency which corresponds to a vibration frequency of the acoustic element. Using such a method, the acoustic element 1000 may convert a received echoed ultrasonic signal to an electrical signal.

Therefore, the acoustic element 1000 may be implemented as a magnetostrictive ultrasonic transducer which uses the magnetostrictive effect of a magnetic material, and the like, a piezoelectric ultrasonic transducer or a piezoelectric micromachined ultrasonic transducer (pMUT) which uses a piezoelectric effect of a material, and may also be implemented as a capacitive micromachined ultrasonic transducer (hereinafter abbreviated as cMUT) which transmits and receives ultrasonic waves using vibration of hundreds or thousands of micromachined thin films.

As still another embodiment, the acoustic element 1000 may also include a two-dimensional transducer array. When the acoustic element 1000 includes the two-dimensional transducer array, it is possible to perform three-dimensional imaging of an inside of an object.

In addition, even when the acoustic element of the ultrasonic probe 300 is arranged in one dimension, the ultrasonic probe 300 may acquire information on a volume of the inside of the object while mechanically moving the acoustic element arranged in one dimension and transmit an echoed ultrasonic signal capable of generating a three-dimensional ultrasound image to the main body 400.

Figure 3:
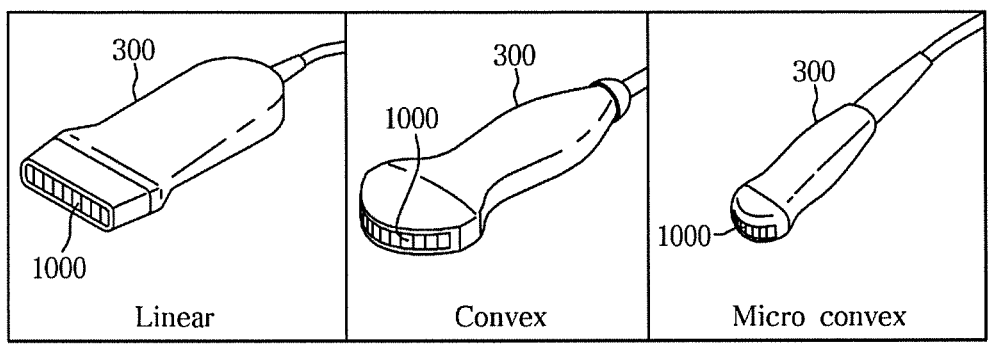
FIG. 3 is a view illustrating internal structures of various types of ultrasonic probes which are classified according to shapes of acoustic elements according to an embodiment of the present invention.

FIG. 3 is a view illustrating internal structures of various types of ultrasonic probes which are classified according to shapes of acoustic elements.

The probes illustrated in FIG. 2 and the first figure of FIG. 3 are linear probes in which linear acoustic elements are linearly arranged.

The probe illustrated in the second figure of FIG. 3 is a convex probe. Since a surface thereof is convex, a fan-shaped image is created. The convex probe is mostly used in examining a wide area such as an abdomen. A fundamental operation principle of the ultrasonic probe 300 is the same as the linear probe.

The probe illustrated in the third figure of FIG. 3 is a micro convex probe which is designed in a small size to facilitate examination of a narrow area while still having the effects of the convex probe.

Figure 4:
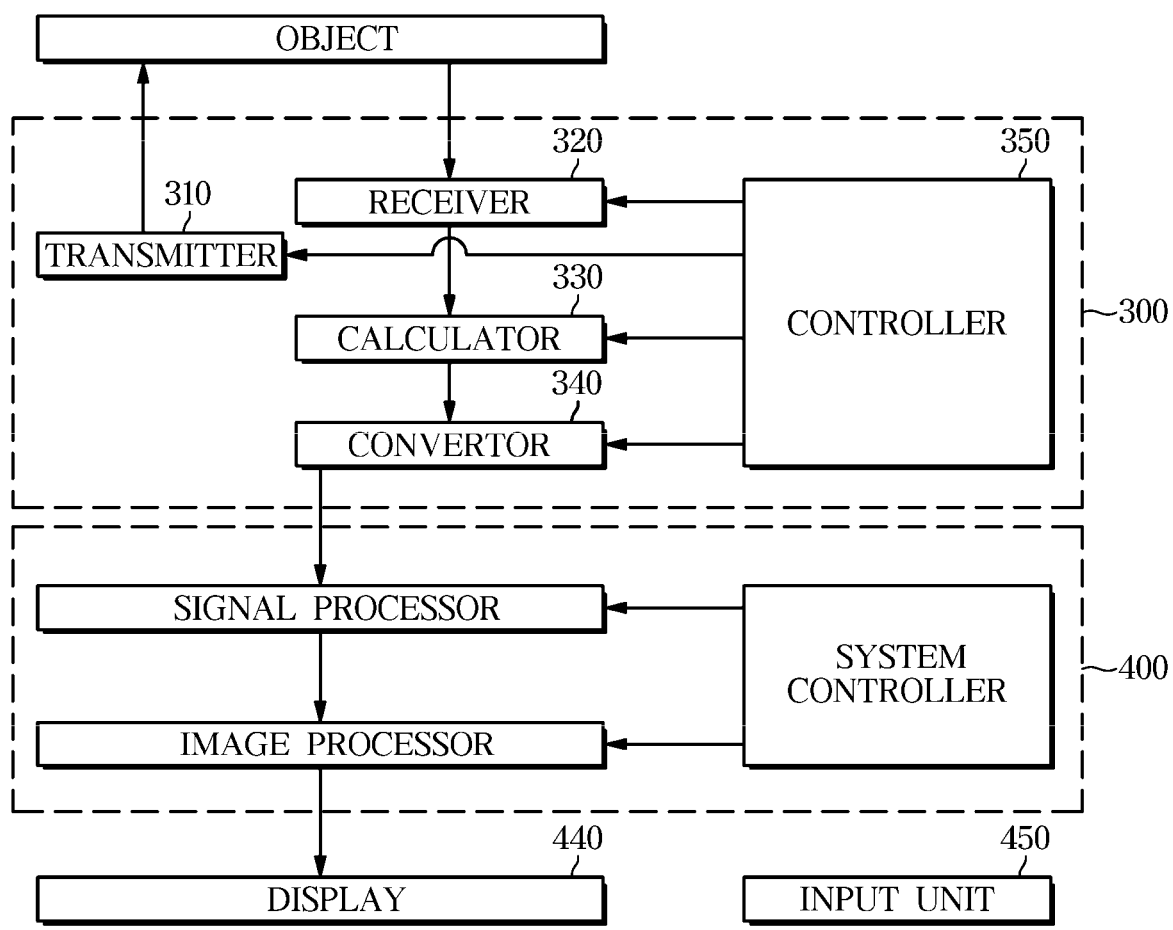
FIG. 4 is a block diagram illustrating an internal configuration of the ultrasonic diagnostic apparatus which includes the ultrasonic probe according to an embodiment of the present invention.

FIG. 4 is a block diagram illustrating an internal configuration of the ultrasonic diagnostic apparatus 1 which includes the ultrasonic probe 300 according to an embodiment of the present invention.

Referring to FIG. 4, the ultrasonic diagnostic apparatus 1 may include a transmitter 310, a receiver 320, a calculator 330, a convertor 340, and a controller 350. The calculator 330, the converter 340, and the controller 350 may be integrated in a system-on-chip (SOC) embedded in the diagnostic apparatus 1. However, since a plurality of SOCs may be embedded in the diagnostic apparatus 1 instead of only one SOC being present therein, the calculator 330, the converter 340, and the controller 350 are not limited to only being integrated in one SOC.

The transmitter 310 may transmit an ultrasonic signal to an object corresponding to a control command of the user. The transmitter 310 may convert an electrical signal to an ultrasonic signal using an acoustic element 1000, which is implemented using various methods, and may transmit the converted ultrasonic signal to the object.

According to an embodiment, when the acoustic element 1000 is implemented as a piezoelectric ultrasonic transducer element, the transmitter 310 may convert an electrical signal to an ultrasonic signal through a piezoelectric layer.

Specifically, the piezoelectric layer may include a piezoelectric material. An electrode for connecting an electrical signal may be formed in the piezoelectric material and may convert an ultrasonic signal to an electrical signal and vice versa. An internal configuration of the ultrasonic probe 300 implemented using the piezoelectric ultrasonic transducer will be described in detail below.

As another example, when the acoustic element 1000 is implemented as a Piezoelectric Micromachined Ultrasonic Transducer (pMUT), the transmitter 310 may convert an electrical signal to an ultrasonic signal through a piezoelectric membrane which is thinner than the piezoelectric layer and may transmit the converted ultrasonic signal to the object.

The operation principles and configurations of the ultrasonic diagnostic apparatus 1 including the ultrasonic probe 300 have been described above. Hereinafter, structural problems of a conventional ultrasonic probe and features of the present invention will be described in detail with reference to the accompanying drawings.

Figure 5:
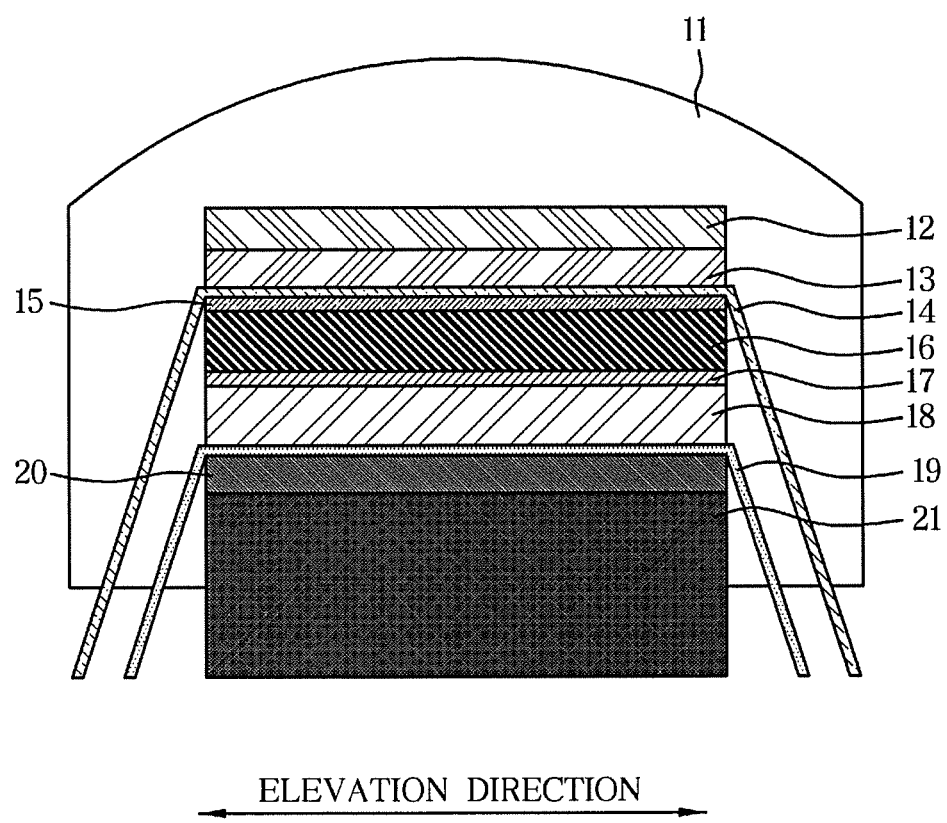
FIG. 5 is a view illustrating a laminated structure of an acoustic element of an ultrasonic probe according to a related art.

FIG. 5 is a view illustrating a laminated structure of an acoustic element inside an ultrasonic probe according to a related art.

Generally, an ultrasonic probe includes a piezoelectric material 16 configured to directly convert an electrical signal to an ultrasonic signal and vice versa and electrodes 15 and 17 formed for electrical signal connection with the piezoelectric material 16 in a predetermined section of an outer circumferential surface of the piezoelectric material 16. The piezoelectric material 16 and the electrodes 15 and 17 may also be collectively referred to as a piezoelectric layer.

In addition, the ultrasonic probe includes matching layers 12 and 13 disposed at an upper portion of the piezoelectric material 16 and configured to reduce an acoustic impedance difference between the object (not illustrated) and the piezoelectric material 16 so that an ultrasonic signal is more smoothly transmitted to the object (not illustrated).

In addition, the ultrasonic probe may include an enhanced layer 18 disposed at a lower portion of the piezoelectric material 16 and configured to reflect an ultrasonic signal, which is transmitted in a direction opposite to the object (not illustrated), and amplify transmission of the ultrasonic signal to the object (not illustrated).

The matching layers 12 and 13 may be formed of a single layer, formed of two matching layers, i.e., a first matching layer 13 and a second matching layer 12, as illustrated in FIG. 5, or formed of three or more matching layers.

In addition, the ultrasonic probe includes a backing layer 20 and a backing block 21 disposed at a lower portion of the piezoelectric material 16 or the enhanced layer 18 and configured to attenuate an ultrasonic signal transmitted in a direction opposite to the object (not illustrated). The backing layer 20 and the backing block 21 include a backing material.

In addition, the ultrasonic probe includes printed circuit boards 14 and 19 electrically connected to the electrode 15 at an upper portion of the piezoelectric material 16 and the electrode 17 at a lower portion of the piezoelectric material 16.

The printed circuit boards are divided into a ground printed circuit board 14 and a signal printed circuit board 19 according to a polarizing direction of the piezoelectric material 16 and electrical signal connection therewith and may be formed of flexible printed circuit boards (FPCB) having flexibility for mechanical assembly in an internal structure of the ultrasonic probe. The printed circuit boards 14 and 19 are inserted into a laminated structure inside the ultrasonic probe to be parallel to the piezoelectric material 16.

In addition, the ultrasonic probe includes an acoustic lens 11 disposed at an upper portion of the second matching layer 12 and configured to come in direct contact with the object (not illustrated). The acoustic lens 11 may focus a transmitted ultrasonic signal to a predetermined position in an elevation direction of the ultrasonic probe.

In the case of the ultrasonic probe of the related art according to FIG. 5, the ground printed circuit board 14 and the signal printed circuit board 19 are interposed inside the laminated structure of the acoustic element of the ultrasonic probe to be parallel to the piezoelectric material 16 at the upper portion or lower portion of the piezoelectric material 16.

However, in such a case, since the printed circuit boards 14 and 19 are disposed inside the laminated structure of the acoustic element of the ultrasonic probe, there is a problem in that acoustic characteristics of the ultrasonic probe are highly affected by materials and thicknesses of the printed circuit boards 14 and 19.

Particularly, an influence of thicknesses of copper (Cu) foils of the printed circuit boards 14 and 19 on the acoustic characteristics increases as a frequency used in the ultrasonic probe becomes higher, and accordingly, there is a problem in that a limitation exists in further reducing thicknesses of the Cu foils of the printed circuit boards 14 and 19 due to a problem in terms of manufacture and processing of the printed circuit boards 14 and 19 or the ultrasonic probe.

Figure 6:
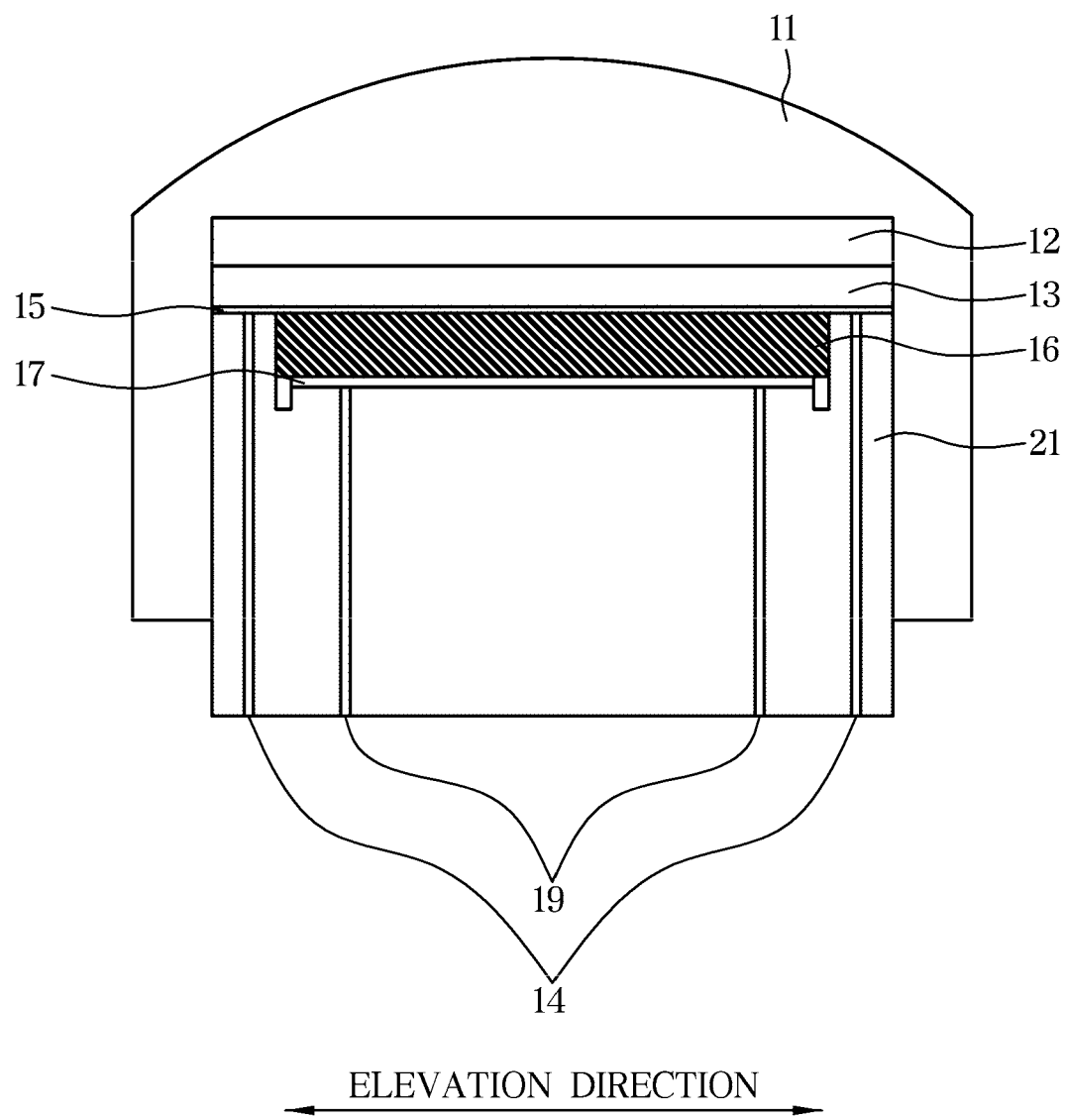
FIG. 6 is a view illustrating a laminated structure of an acoustic element of an ultrasonic probe according to another related art.

FIG. 6 is a view illustrating a laminated structure of an acoustic element inside an ultrasonic probe according to another related art.

In the case of the ultrasonic probe according to FIG. 6, unlike the ultrasonic probe according to FIG. 5 in which the printed circuit boards 14 and 19 are interposed within the laminated structure of the ultrasonic probe in parallel, the printed circuit boards 14 and 19 are disposed to be perpendicular to the laminated structure.

That is, referring to FIG. 6, it can be seen, while the printed circuit boards 14 and 19 are disposed to be perpendicular to the laminated structure of the acoustic element, the signal printed circuit board 19 is electrically connected to the electrode 17 at the lower portion of the piezoelectric material 16, and the ground printed circuit board 14 is electrically connected to the electrode 15 at the upper portion of the piezoelectric material 16.

However, in the case of the ultrasonic probe according to FIG. 6, since the printed circuit boards 14 and 19 are disposed inside the backing block 21, connection between the printed circuit boards 14 and 19 and the piezoelectric material 16 may become unstable. Therefore, there is a problem in that a process of manufacturing the ultrasonic probe becomes complex in order to ensure stable electrical connection.

In addition, due to the structural characteristic in which the printed circuit boards 14 and 19 are disposed inside the backing block 21, a problem in that the printed circuit boards 14 and 19 contract or expand according to a change in temperature or humidity may occur.

Therefore, the present invention has been devised to solve such conventional problems. In the present invention, a printed circuit board, which is an electrical connection means of a piezoelectric material, is disposed outside a laminated structure of an acoustic element and outside a backing material so that the printed circuit board does not affect acoustic characteristics, a process of manufacturing an ultrasonic probe is further simplified, and a failure in the manufacturing process is prevented. Features of the present invention will be described in detail below with reference to the accompanying drawings.

For describing various embodiments according to the present invention, only some of the elements of the ultrasonic probe have been illustrated in the accompanying drawings in order to clarify the gist of the present invention. One or more other elements which are evident to those of ordinary skill in the art to which the present invention pertains but are not illustrated may exist.

Figure 7:
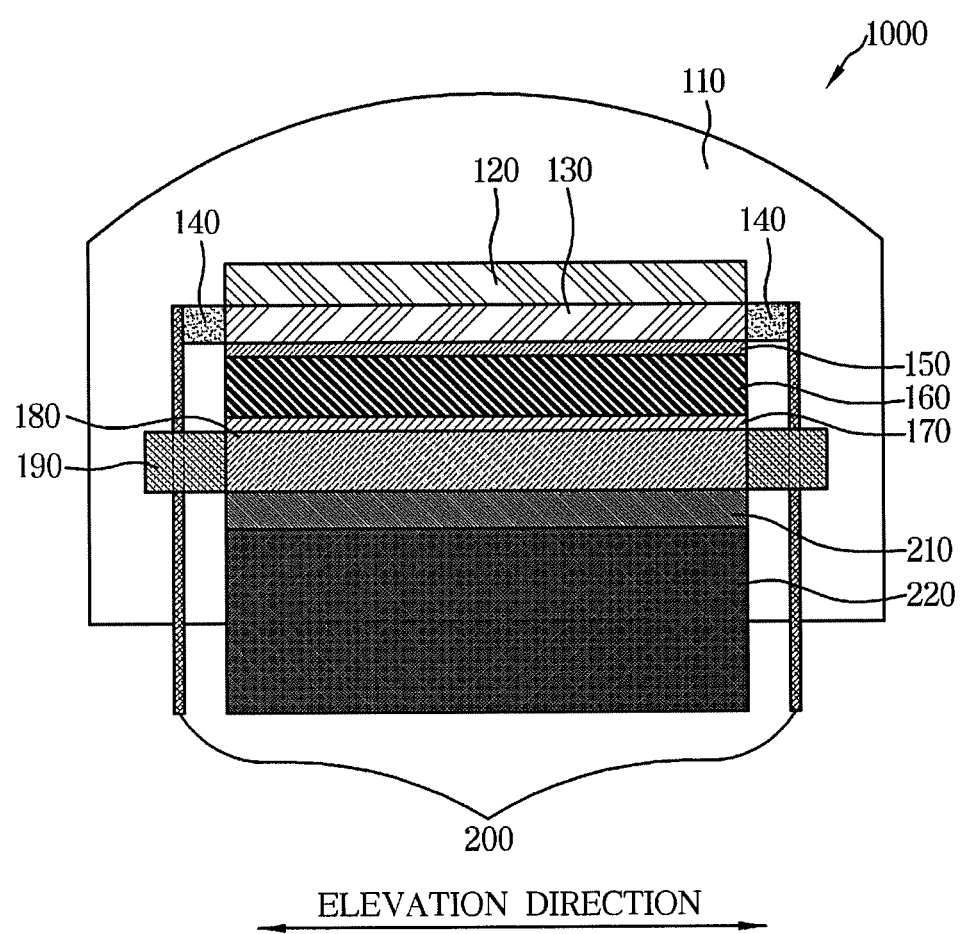
FIG. 7 is a view illustrating a laminated structure of an acoustic element of the ultrasonic probe according to an embodiment of the present invention.

FIG. 7 is a view illustrating a laminated structure of an acoustic element of the ultrasonic probe according to an embodiment of the present invention.

Referring to FIG. 7, an acoustic element 1000 inside an ultrasonic probe according to an embodiment of the present invention may include an acoustic lens 110, matching layers 120 and 130, a first connector 140 disposed on at least one side of the matching layers, a piezoelectric material 160, an upper electrode 150 and a lower electrode 170 electrically separately formed at an upper portion and a lower portion of the piezoelectric material 160 respectively, a conductive member 180 disposed below the lower electrode 170 and having electrical conductivity, a second connector 190 disposed on at least one side of the conductive member 180, a backing layer 210 disposed below the conductive member 180, and a backing block 220 disposed below the backing layer 210.

In addition, although a state in which the first connector 140 is disposed at both sides of the first matching layer 130 and the second connector 190 is disposed at both sides of the conductive member 180 is illustrated in FIG. 7, the first connector 140 and the second connector 190 may not necessarily be disposed at both sides. For example, the first connector 140 may be disposed at only one side of the first matching layer 130, and the second connector 190 may be disposed at only one side of the conductive member 180.

In the case of the acoustic element 1000 according to FIG. 7, the acoustic lens 110 configured to come in direct contact with an object (not illustrated) may be disposed at an upper portion of the second matching layer 120. The acoustic lens 110 may serve to focus a transmitted ultrasonic signal in an elevation direction of the acoustic element 1000.

The matching layers 120 and 130 may be disposed at the upper portion of the piezoelectric material 160 and serve to reduce an acoustic impedance difference between the object (not illustrated) and the piezoelectric material 160.

The matching layers 120 and 130 may be formed as a single layer or formed as a plurality of layers as illustrated in FIG. 7. When the matching layers 120 and 130 are formed as a plurality of layers, the acoustic impedance difference between the object (not illustrated) and the piezoelectric material 160 may be reduced in further subdivided stages, and an ultrasonic signal may be more smoothly transmitted to the object (not illustrated). When the matching layers 120 and 130 are formed as two layers, the second matching layer 120 and the first matching layer 130 may be separately formed as illustrated in FIG. 7.

When the matching layers 120 and 130 are formed as two layers as illustrated in FIG. 7, the first matching layer 130 may be formed of a material having electrical conductivity.

When the first matching layer 130 is formed of a material which does not have electrical conductivity, an electrode may be formed at an outer circumferential surface of the first matching layer 130 using a sputtering method in order to ensure stable electrical connection between the matching layers 120 and 130 and the first connector 140 or a printed circuit board 200. A method of forming the electrode is not limited thereto, and various other methods may be applied as long as the electrode may be formed using the method.

The first connector 140 may be disposed on at least one side of the first matching layer 130. The first connector 140 may be disposed to extend longer than a length of the piezoelectric material 16 in a direction perpendicular to the laminated structure of the acoustic element 1000.

The first connector 140 may be coupled to the printed circuit board 200 in the form in which the first connector 140 passes through the printed circuit board 200 or in the form in which the printed circuit board 200 is attached to an outside of the first connector 140 as illustrated in FIG. 7. In addition, the first connector 140 and the printed circuit board 200 which are coupled to each other may be electrically coupled.

In addition, the first connector 140 may be formed of the same material as the first matching layer 130 and be integrally formed with the first matching layer 130.

In addition, the first connector 140 may be formed of a Cu foil layer of the printed circuit board 200 which protrudes to a certain thickness from the printed circuit board 200 toward the first matching layer 130 or may be formed of a separate electrical connection means such as a gasket, a ground extending film, or a conductive elastomer to facilitate electrical coupling between the printed circuit board 200 and the first matching layer 130.

In addition, the first connector 140 may be integrally formed with the first matching layer 130, be a Cu foil layer protruding from the printed circuit board 200, or be a separate electrical connection means as described above. Also, the first connector 140 may also be a combination of two or more of the above.

In addition, the first connector 140 may be coupled to the first matching layer 130 and/or the printed circuit board 200 using an adhesive member (not illustrated), and the adhesive member (not illustrated) may include any one or more of a tape, an adhesive, or epoxy.

When adhered using a tape, the adhesion may be performed using at least one of an anisotropic conductive tape, an isotropic conductive tape, and a non-conductive conductive tape. When an adhesive or epoxy is used, the adhesion may be performed using at least one of an anisotropic conductive adhesive or epoxy, an isotropic conductive adhesive or epoxy, and a non-conductive adhesive or epoxy.

The piezoelectric material 160 is disposed at a lower portion of the first matching layer 130 and serves to directly convert an electrical signal to an ultrasonic signal and vice versa. In addition, the electrodes 150 and 170 may be formed at an outer circumferential surface of the piezoelectric material 160 for electrical signal connection with the piezoelectric material 160, and the upper electrode 150 and the lower electrode 170 may be formed in various sections of the outer circumferential surface of the piezoelectric material 160 according to an electrical signal connection method of the piezoelectric material 160.

In addition, the piezoelectric material 160, the upper electrode 150, and the lower electrode 170 may also be collectively referred to as a piezoelectric layer.

When an electrical signal is applied to the piezoelectric material 160, the piezoelectric material 160 serves to cause a mechanical vibration and generate an ultrasonic signal. Conversely, when an echoed ultrasonic signal is received, the piezoelectric material 160 serves to, in reverse, convert the received signal to an electrical signal.

Therefore, in order to enable such interconversions, the piezoelectric material 160 may be formed of at least one of piezoelectric materials that include manganese-substituted-lead-zirconium-titanate (PZMT) single crystals consisting of lead zirconate titanate (PZT) ceramics and a solid solution of lead magnesium niobate and lead titanate, lead zincate niobate titanate (PZNT) single crystals consisting of a solid solution of lead zinc niobate and lead titanate or the like. A structure of the piezoelectric material 160 may also be formed of a single layer or a multi-layer laminated structure.

The conductive member 180 may be disposed at the lower portion of the piezoelectric material 160 and be formed of a material having electrical conductivity. The conductive member 180 may serve to reflect an ultrasonic signal which is transmitted toward the lower portion of the piezoelectric material 160, which is a direction opposite to the object (not illustrated), and amplify transmission of the ultrasonic signal toward the object (not illustrated).

Therefore, in order to play such roles, the conductive member 180 may be typically formed of a tungsten material (WC). However, embodiments are not limited thereto, and the conductive member 180 may be formed of any material as long as the material is capable of performing functions similar to those described above.

When the conductive member 180 is formed of a material which does not have electrical conductivity, an electrode (not illustrated) may be formed at an outer circumferential surface of the conductive member 180 using a sputtering method or the like. A method of forming the electrode is not limited to the sputtering method, and the electrode may be formed using various other methods similar thereto.

The second connector 190 may be disposed on at least one side of the conductive member 180 and may be disposed to extend toward the outside of the piezoelectric material 160 by a predetermined length from the piezoelectric material 160. Therefore, the second connector 190 may be disposed in a state of protruding outward in the laminated structure of the ultrasonic probe.

The second connector 190 may be disposed to be perpendicular to the laminated structure of the acoustic element 1000 and coupled to the printed circuit board 200, which is disposed outside the laminated structure, at the same time.

As illustrated in FIG. 7, the second connector 190 may be coupled in the form in which the second connector 190 passes through the printed circuit board 200 or is attached to the outside of the printed circuit board 200. The second connector 190 and the printed circuit board 200 which are coupled to each other may be electrically coupled.

In addition, the second connector 190 may be formed of the same material as the conductive member 180, and may be integrally formed with the conductive member 180 or formed of a Cu foil layer of the printed circuit board 200 protruding from the printed circuit board 200 toward the conductive member 180. In addition, the second connector 190 may be formed of a separate electrical connection means for electrical coupling to the printed circuit board 200 and the conductive member 180.

The second connector 190 may be integrally formed with the conductive member 180, be a Cu foil protruding from the printed circuit board 200, or be a separate electrical connection means as described above. Also, the second connector 190 may also be a combination of two or more of the above.

In addition, the second connector 190 may be coupled to the conductive member 180 and/or the printed circuit board 200 using an adhesive member (not illustrated), and the adhesive member (not illustrated) may be any one or more of a tape, an adhesive, or epoxy.

When adhered using a tape, the adhesion may be performed using at least one of an anisotropic conductive tape, an isotropic conductive tape, and a non-conductive tape. When an adhesive or epoxy is used, the adhesion may be performed using at least one of an anisotropic conductive adhesive or epoxy, an isotropic conductive adhesive or epoxy, and a non-conductive adhesive or epoxy.

The printed circuit board 200 may be disposed outside the laminated structure while being perpendicular to the laminated structure of the acoustic element 1000.

As illustrated in FIG. 7, the printed circuit board 200 may be disposed at both sides of the laminated structure of the acoustic element 1000, and unlike FIG. 6, may be disposed in only one direction. Therefore, the number of printed circuit boards 200 is not limited to a specific number.

The printed circuit board 200 may be coupled perpendicular to a side of the first connector 140, which is coupled to at least one side of the first matching layer 130, and coupled to the second connector 190, which is coupled to at least one side of the conductive member 180, at the same time. The printed circuit board 200, the first connector 140, and the second connector 190 may be electrically coupled.

According to a polarizing direction of the piezoelectric material 160, any one of the second connector 190 and the first connector 140 may become an electrical signal connection means of the piezoelectric material 160, and the other may become an electrical ground connection means of the piezoelectric material 160. In the case of the present invention, a direction of the electrical signal or ground connection of the piezoelectric material 160 is not limited to a specific direction.

The printed circuit board 200 may include a FPCB having flexibility for mechanical assembly in an internal structure of the ultrasonic probe.

The backing layer 210 and the backing block 220 which are disposed at the lower portion of the conductive member 180 may serve to attenuate an ultrasonic signal transmitted in a direction opposite to the object (not illustrated), and according to a method of manufacturing the ultrasonic probe, only the backing block 220 may be present without the backing layer 210.

A fundamental structure of the acoustic element 1000 inside the ultrasonic probe of the present invention has been described above with reference to FIG. 7. Hereinafter, various embodiments of the present invention will be described with reference to the drawings.

FIG. 8 is a view illustrating a state of the printed circuit board 200 coupled to the second connector 190 or the first connector 140 according to the embodiment illustrated in FIG. 7. (a) of FIG. 8 illustrates a printed circuit board 200 having a plurality of holes 201, and (b) of FIG. 8 illustrates a printed circuit board 200 having a slot 202.

Referring to FIG. 8, since the second connector 190 and the printed circuit board 200 may be coupled using a method in which the second connector 190 passes through the printed circuit board 200, the printed circuit board 200 may include at least one hole 201 or at least one slot 202 which is disposed at a position at which the printed circuit board 200 is coupled to the second connector 190 to facilitate the coupling therebetween.

The second connector 190 and the hole 201 or the slot 202 may be physically directly coupled to each other or indirectly coupled to each other while a conductive or non-conductive connecting member (not illustrated) is interposed therebetween. The coupling method is not limited to a specific method.

In addition, the size and shape of the hole 201 or the slot 202 is not limited to a specific size and a specific shape as long as the printed circuit board 200 is allowed to be stably electrically coupled. An inner wall of the hole 201 or the slot 202 may be plated for efficient electric conduction according to a method of manufacturing the printed circuit board 200.

According to a configuration method, when the acoustic element 1000 is divided into a plurality of acoustic elements 1000, the second connector 190 and the printed circuit board 200 may be coupled using a method in which the second connector 190 and the printed circuit board 200 are fitted using the plurality of holes 201 as illustrated in FIG. 8(a).

In another method, when the acoustic element 1000 is not divided into a plurality of acoustic elements 1000 in the process of manufacturing the ultrasonic probe 300, the second connector 190 and the printed circuit board 200 may be coupled using a method in which the second connector 190 and the printed circuit board 200 are integrally fitted using the slot 202 as illustrated in FIG. 8(b). In such a case, the acoustic element 1000 may be divided into a plurality of acoustic elements 1000 after the second connector 190 and the printed circuit board 200 are coupled thereto.

FIG. 9 is a view illustrating a laminated structure of an acoustic element 1000 of an ultrasonic probe 300 according to still another embodiment of the present invention, (a) and (b) of FIG. 10 are views illustrating states of a printed circuit board 200 according to the embodiment illustrated in FIG. 8, and FIG. 11 is a view illustrating a state in which the second connector 190 is inserted into the printed circuit board 200 according to the embodiment illustrated in FIG. 9.

Referring to FIG. 9, in the case of the acoustic element 1000 of the ultrasonic probe 300 according to FIG. 8, the overall structure and laminating order are the same as those of the acoustic element 1000 of the ultrasonic probe 300 illustrated in FIG. 6, but there is a difference (portion "a" in FIG. 8) in terms of a method in which the second connector 190 and the printed circuit board 200 are coupled.

That is, although the second connector 190 is coupled by passing through the printed circuit board 200 in the case of the laminated structure of the acoustic element 1000 according to FIG. 7, the printed circuit board 200 is coupled by being attached to an outer wall of the second connector 190 in the case of the laminated structure of the acoustic element 1000 according to FIG. 9.

Therefore, as illustrated in FIG. 10(a), a plurality of holes 203 may be disposed at a portion of the printed circuit board 200 coupled to the second connector 190 in order to facilitate the coupling therebetween. In such a case, the second connector 190 may be coupled by being attached to an outer wall of the printed circuit board 200, and for the electrical coupling between the second connector 190 and the printed circuit board 200, a plurality of lands 204 which are electrically connected to the printed circuit board 200 may be included in the holes 203.

In addition, a plurality of pads 205, instead of the plurality of holes 203, may be included in the printed circuit board 200 to facilitate the coupling. The plurality of holes 203 and lands 204 and/or the plurality of pads 205 may be electrically coupled to the second connector 190.

The methods and forms in which the second connector 190 and the printed circuit board 200 are coupled to each other have been described above with reference to FIG. 10. Such methods and forms may be identically applied to the case in which the first connector 140 and the printed circuit board 200 are coupled to each other.

That is, when the first connector 140 of FIGS. 7 and 9 is coupled by being attached to the outer wall of the printed circuit board 200, the holes 203 and the lands 204 and/or the pads 205, which are electrically connected to the circuit configuration of the printed circuit board 200, may be included in the printed circuit board 200 in order to facilitate the coupling. In this way, the first connector 140 and the printed circuit board 200 may be electrically connected.

In addition, the holes 203 and the lands 204 and/or the pads 205 of the printed circuit board 200 connected to the second connector 190 or the first connector 140 may be formed to have a step difference with each other according to a lamination configuration in order to form a circuit of the printed circuit board 200.

FIG. 11 is a view illustrating yet another embodiment in which the second connector 190 and the printed circuit board 200 are coupled to each other using an engaging portion of the printed circuit board 200 according to the embodiment illustrated in FIG. 9.

Referring to FIG. 11, it can be seen that a portion of the second connector 190 is coupled by being inserted into an engaging portion 206 which is formed to have a predetermined depth from an outer wall of the printed circuit board 200.

When coupled as illustrated in FIG. 11, since the portion of the second connector 190 is inserted into the engaging portion 206 having a predetermined depth from the outer wall of the printed circuit board 200, the second connector 190 and the printed circuit board 200 may be more firmly coupled to each other, and thus it is possible to configure an acoustic element 1000 which is more stable mechanically.

FIGS. 12 to 14 are views illustrating laminated structures of an acoustic element 1000 according to yet another embodiment of the present invention.

The acoustic element 1000 according to FIG. 12 may include an acoustic lens 110, a second matching layer 120, a first matching layer 130, a piezoelectric material 160 disposed at a lower portion of the first matching layer 130, electrodes 150 and 170 electrically separately formed at an upper portion and a lower portion of the piezoelectric material 160 respectively, a backing layer 210 disposed below the lower electrode 170, and a backing block 220 disposed below the backing layer 210.

Unlike the acoustic element 1000 according to FIG. 7, the acoustic element 1000 according to FIG. 12 does not include the conductive member 180 disposed below the piezoelectric material 160 and the second connector 190 coupled to the conductive member 180.

Instead, in the case of the acoustic element 1000 according to FIG. 12, the backing layer 210 may be disposed right below the piezoelectric material 160, and a third connector 230 configured to play a similar role to the second connector 190 of FIG. 7 may be disposed on at least one side of the backing layer 210. In addition, similar to FIG. 7, a printed circuit board 200 may be disposed outside the acoustic element 1000 in a direction perpendicular to the laminated structure of the acoustic element 1000 and be coupled to a first connector 140 and the third connector 230 at the same time.

The backing layer 210 of the acoustic element 1000 according to FIG. 12 may be formed of a material having electrical conductivity or formed of a material which does not have electrical conductivity.

When the backing layer 210 is formed of a material which does not have electrical conductivity, an electrode (not illustrated) may be formed at an outer circumferential surface of the backing layer 210 using a sputtering method or the like. A method of forming the electrode is not limited to the sputtering method, and the electrode may be formed using various other methods similar thereto.

In the case of the acoustic element 1000 according to FIG. 12, the printed circuit board 200 may be coupled to the first connector by being attached to the outside of the first connector 140 and may be coupled to the third connector 230 by the third connector 230 passing through the printed circuit board 200.

Therefore, the printed circuit board 200 may be coupled according to the method shown in FIGS. 10 and 11 when being attached to the first connector 140 and coupled according to the method shown in FIG. 8 when being coupled to the third connector 230. In order to facilitate such coupling, the printed circuit board 200 may include a plurality of holes 203 and lands 204 and/or a plurality of pads 205 as illustrated in FIG. 10, or the printed circuit board 200 may include an engaging portion 206, into which a portion of the third connector 230 is inserted, that is formed to have a predetermined depth from an outer wall of the printed circuit board 200 as illustrated in FIG. 11.

When the third connector 230 is coupled by passing through the printed circuit board 200, the printed circuit board 200 may include a plurality of holes 201 or one or more slots 202 so that the third connector 230 may pass through the printed circuit board 200. Characteristics and coupling methods of the plurality of holes 201 or slots 202 are the same as those described above with reference to FIGS. 8 to 10.

In the case of FIG. 12, the printed circuit board 200 is illustrated as being coupled to the first connector 140 by being attached to the outside of the first connector 140 and being coupled to the third connector 230 by the third connecting 230 passing through the printed circuit board 200. However, unlike that, the printed circuit board 200 may also be coupled to the first connector 140 by the first connector 140 passing through the printed circuit board 200 and be coupled to the third connector 230 by being attached to the outside of the third connector 230.

FIG. 13 is a view illustrating a laminated structure of an acoustic element 1000 according to yet another embodiment of the present invention.

Referring to FIGS. 7 and 13, in the case of the acoustic element 1000 of FIG. 13, a fundamental laminated structure is the same as the laminated structure of the acoustic element 1000 illustrated in FIG. 7, but there is a difference in terms of a structure of a first matching layer 130.

In the case of the acoustic element 1000 according to FIG. 7, the first connector 140 is disposed at the outside of the first matching layer 130, and the first connector 140 is coupled to the printed circuit board 200. However, in the case of the acoustic element 1000 according to FIG. 13, the first connector 140 does not exist, and the first matching layer 130 extends toward both sides in a direction perpendicular to the laminated structure. Therefore, the first matching layer 130 extending in such a way may be coupled to the printed circuit board 200 by passing through the printed circuit board 200.

Of course, coupling may be performed by the printed circuit board 200 being attached to the outside of extensions of the first matching layer 130 and the outside of the second connector 190 also in the acoustic element 1000 according to FIG. 13.

FIG. 14 is a view illustrating a laminated structure of an acoustic element 1000 according to yet another embodiment of the present invention.

In the case of the acoustic element 1000 according to FIG. 14, the structure of the acoustic element is the same as that of the acoustic element 1000 illustrated in FIG. 7, but a connecting member 240 and a supporter 250 have been added to reinforce coupling between the printed circuit board 200 and the acoustic element 1000.

The connecting member 240 is used to further reinforce coupling between the printed circuit board 200 and the second connector 190. The connecting member 240 may be formed of a tape and/or an adhesive.

When a tape is used, the connecting member 240 may include at least one of an anisotropic conductive tape, an isotropic conductive tape, and a non-conductive tape, and when an adhesive member is used, the connecting member 240 may include at least one of an anisotropic conductive adhesive, an isotropic conductive adhesive, and a non-conductive adhesive.

Since the connecting member 240 reinforces, at a position at which electrical connection between the printed circuit board 200 and the second connector 190 is performed, the electrical connection and mechanical connection therebetween, the acoustic element 1000 may be more stably configured.

Generally, the supporter 250 may be used in coupling the printed circuit board 200 to the backing layer 210 and/or the backing block 220.

The supporter 250 may be configured by including any one or more of various mechanical engaging means including a bolt, a clip, a gasket, a spacer, and a pin.

In addition, since the supporter 250 supports coupling between the printed circuit board 200 and the backing layer 210 and/or backing block 220 to be mechanically firmer, the acoustic element 1000 may be more stably configured.

In the case of FIG. 14, the connecting member 240 is illustrated as being disposed at a combination of the second connector 190 and the printed circuit board 200. However, embodiments are not limited thereto, and the connecting member 240 may be disposed together with the first connector 140, the second connector 190, or the third connector 230 when the first connector 140, the second connector 190, or the third connector 230 is coupled to the printed circuit board 200 to further reinforce the electrical connection and mechanical connection as illustrated in FIGS. 7, 9, and 12 to 14.

FIG. 15 is a view illustrating various states of a printed circuit board 200 according to yet another embodiment of the present invention.

As described above, arrays of acoustic elements in an ultrasonic probe 300 may be configured as a convex type instead of a linear type. Therefore, when the arrays of acoustic elements are configured as the convex type, the printed circuit board 200 may also be configured as the convex type accordingly.

The printed circuit boards 200 illustrated in (a) and (b) of FIG. 15 have the same features as the printed circuit board 200 illustrated in (a) and (b) of FIG. 8 except that upper portions of the printed circuit boards 200 are configured as curved surfaces.

That is, the printed circuit board 200 of (a) of FIG. 15 may include a plurality of holes 203 and lands 204, and the printed circuit board 200 of (b) of FIG. 15 may include a plurality of pads 205.

As illustrated in FIG. 15(c), the printed circuit board 200 may include a concave-convex portion 209 formed at an upper end of the printed circuit board 200. That is, when any one of the first connector 140, the second connector 190, and the third connector 230 of the acoustic element 1000 divided into a plurality of acoustic elements 1000 is coupled to the printed circuit board 200 by being fitted thereto, the printed circuit board 200 may include the concave-convex portion 209 in order to facilitate such coupling.

Various configurations and features of the present invention have been described above with reference to various drawings. In the case of the present invention, unlike the ultrasonic probe of the related art, a printed circuit board is not inserted within a laminated structure of an acoustic element, is not included inside a backing layer, and is disposed outside the laminated structure, it is possible to prevent the printed circuit board from affecting acoustic characteristics.

Features of the present invention have been described above using only a few embodiments and drawings, but those of ordinary skill in the art should be able to make various modifications and changes to the above description. For example, a suitable result may be achieved even if the above-described techniques are performed in an order different from that described above, or the above-described elements such as systems, structures, devices, and circuits are coupled or combined in forms different from those described above within an equivalent scope or substituted by other elements or their equivalents.

Therefore, the other implementations, other embodiments, and equivalents of the claims belong to the scope of the claims below.

The invention claimed is:

1. An ultrasonic probe comprising:
a piezoelectric layer;
a matching layer disposed at an upper portion of the piezoelectric layer;
a first connector disposed to extend from and protrude from at least one side of the matching layer, and integrally formed with the matching layer;
a conductive member disposed at a lower portion of the piezoelectric layer;
a second connector disposed to extend from and protrude from at least one side of the conductive member, and integrally formed with the conductive member;
a backing layer disposed below the conductive member; and
a printed circuit board disposed outside a laminated structure including the piezoelectric layer, the matching layer, the conductive member and the backing layer, wherein all of the printed circuit board is disposed to be spaced apart from the laminated structure,
wherein the printed circuit board is electrically connected to the matching layer by being coupled to the first connector, and is electrically connected to the conductive member by being coupled to the second connector,
wherein each of the first connector and the second connector protrudes from a side surface of the laminated structure to the outside of the laminated structure, and passes through the printed circuit board vertically or is vertically attached to a portion of the outer surface of the printed circuit board, and
wherein each of the first connector and the second connector is disposed between the laminated structure and the printed circuit board to space apart the printed circuit board from the laminate structure.

2. The ultrasonic probe of claim 1, wherein the conductive member includes an enhanced layer configured to reflect an acoustic signal.

3. The ultrasonic probe of claim 1, wherein an electrode for electrical conduction is disposed at an outer circumferential surface of the conductive member.

4. The ultrasonic probe of claim 1, wherein the second connector includes the same material as the conductive member.

5. The ultrasonic probe of claim 1, wherein the printed circuit board includes at least one hole or slot through which the second connector passes, and
the hole and the slot are electrically connected to a circuit configuration of the printed circuit board.

6. The ultrasonic probe of claim 1, wherein the printed circuit board further includes a plurality of concave-convex portions to which the second connector is fitted or an engaging portion through which at least a portion of the second connector is inserted into the printed circuit board, and
the concave-convex portions and the engaging portion are electrically connected to the printed circuit board.

7. The ultrasonic probe of claim 1, wherein the printed circuit board includes one or more lands of holes coupled to the second connector,
the lands include copper foil layers larger than the hole along a circumference of the hole at an outer wall of the printed circuit board, and
the lands are electrically connected to a circuit configuration of the printed circuit board.

8. The ultrasonic probe of claim 1, wherein the printed circuit board includes one or more pads coupled to the second connector,
the pads include copper foil layers at an outer wall of the printed circuit board, and
the pads are electrically connected to the printed circuit board.

9. The ultrasonic probe of claim 1, wherein the matching layer includes a non-conductive material, and
an electrode for electrical conduction is disposed at an outer circumferential surface of the non-conductive material.

10. The ultrasonic probe of claim 9, wherein the first connector includes the same material as the matching layer or includes a copper foil layer disposed at an outer wall of the printed circuit board.

11. The ultrasonic probe of claim 10, wherein the first connector is coupled to the matching layer and the outer wall of the printed circuit board using an adhesive member, and
the second connector is coupled to the conductive member and the outer wall of the printed circuit board using an adhesive member.

12. The ultrasonic probe of claim 1, further comprising a supporter coupled to the printed circuit board and configured to support the printed circuit board to be fixed to a side of the laminated structure of the piezoelectric layer, the matching layer, and the conductive member.

* * * * *